(12) United States Patent
Hellgren et al.

(10) Patent No.: US 10,309,943 B2
(45) Date of Patent: Jun. 4, 2019

(54) INFRARED GAS DETECTOR WITH SECONDARY SENSOR

(71) Applicant: INFICON GmbH, Bad Ragaz (CH)

(72) Inventors: Johan Hellgren, Linkoping (SE); Henrik Vennerberg, Linkoping (SE); Fredrik Enquist, Linkoping (SE)

(73) Assignee: INFICON GmbH, Bad Ragaz (CH)

( * ) Notice: Subject to any disclaimer, the term of this patent is extended or adjusted under 35 U.S.C. 154(b) by 0 days.

(21) Appl. No.: 15/771,675

(22) PCT Filed: Oct. 26, 2016

(86) PCT No.: PCT/EP2016/075765
§ 371 (c)(1),
(2) Date: Apr. 27, 2018

(87) PCT Pub. No.: WO2017/072159
PCT Pub. Date: May 4, 2017

(65) Prior Publication Data
US 2018/0321207 A1    Nov. 8, 2018

(30) Foreign Application Priority Data

Oct. 29, 2015  (EP) .................................. 15192135

(51) Int. Cl.
*G01N 33/00* (2006.01)
*G01N 21/35* (2014.01)
(Continued)

(52) U.S. Cl.
CPC ..... *G01N 33/0031* (2013.01); *G01N 21/3504* (2013.01); *G01N 21/61* (2013.01);
(Continued)

(58) Field of Classification Search
CPC ............... G01N 21/3504; G01N 21/61; G01N 33/0022; G01N 33/0031; G01N 33/0062
See application file for complete search history.

(56) References Cited

U.S. PATENT DOCUMENTS 4,507,558 A    3/1985  Bonne
6,469,303 B1*  10/2002  Sun .................... G01N 21/3504
                                              250/338.3
(Continued)

FOREIGN PATENT DOCUMENTS

DE        2532660 A1      2/1977
EP        1621882 A2      2/2006
WO     2012150516 A1     11/2012

OTHER PUBLICATIONS

Takeuchi et al., "Highly Accurate CO2 Gas Sensor Using a Modulation-Type Pyroelectric Infrared Detector", Jpn. J. Appl. Phys., 1993, pp. 221-227, vol. 32:1A, Tokyo, Japan.

*Primary Examiner* — Mark R Gaworecki
(74) *Attorney, Agent, or Firm* — The Webb Law Firm

(57) ABSTRACT

Infrared gas detection system comprising a gas inlet, an infrared gas analyzer connected to the gas inlet and a secondary gas sensor connected to the gas inlet, and an evaluation device evaluating the measurement signals from both the infrared gas analyzer and from the secondary gas sensor, such that a gas is identified only if both the infrared measurement signal and the secondary measurement signal coincide in time.

2 Claims, 1 Drawing Sheet

(51) Int. Cl.
*G01N 21/61* (2006.01)
*G01N 21/3504* (2014.01)

(52) U.S. Cl.
CPC ..... *G01N 33/0022* (2013.01); *G01N 33/0062* (2013.01); *G01N 33/0032* (2013.01)

(56) References Cited

U.S. PATENT DOCUMENTS

| | | |
|---|---|---|
| 7,030,381 B2 | 4/2006 | Kilian et al. |
| 2005/0173635 A1* | 8/2005 | Smith ................ G01N 21/3504 250/339.13 |
| 2011/0141454 A1 | 6/2011 | Henning et al. |
| 2012/0143515 A1* | 6/2012 | Norman ............. G01N 33/0073 702/24 |

* cited by examiner

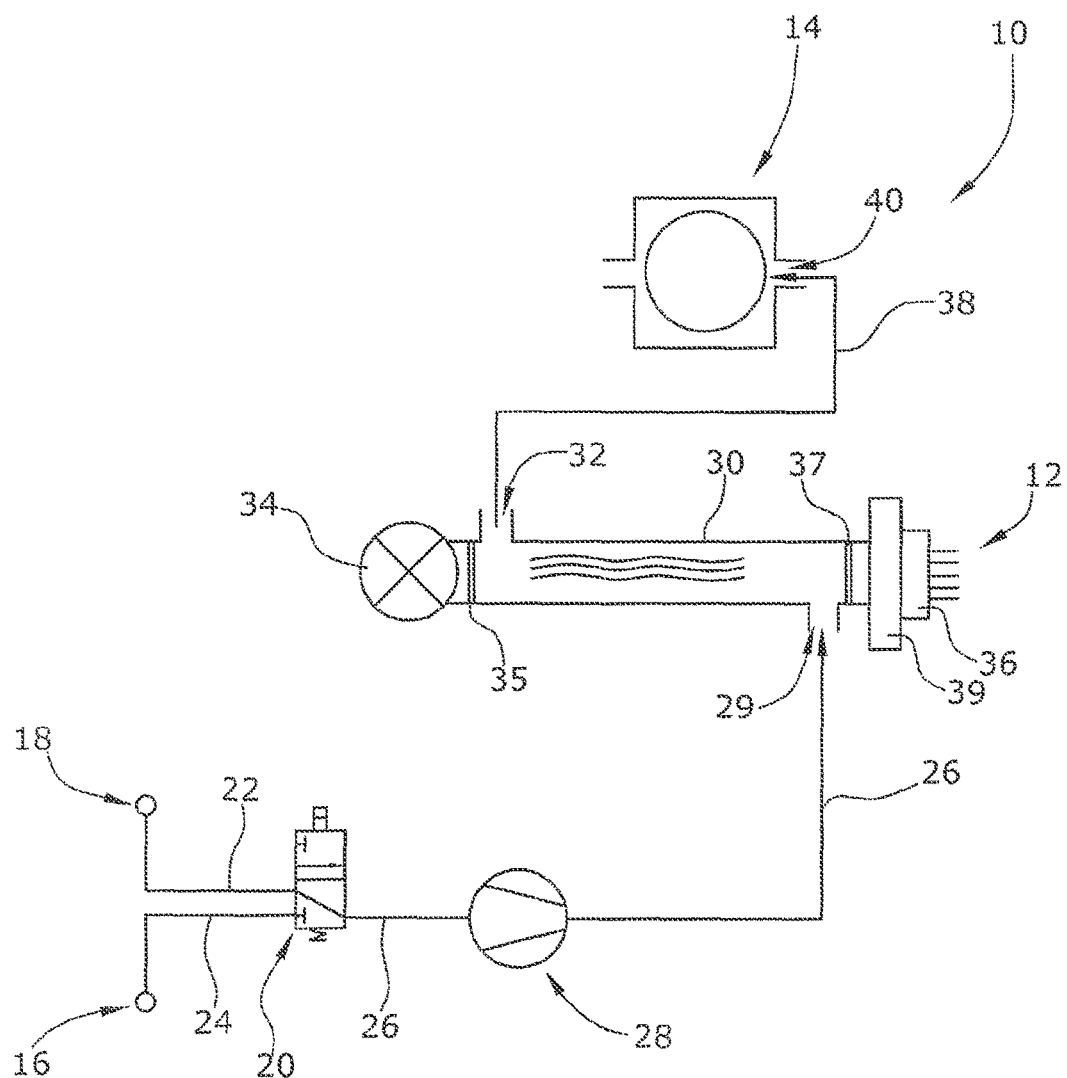

INFRARED GAS DETECTOR WITH SECONDARY SENSOR

CROSS-REFERENCE TO RELATED APPLICATIONS

This application is the United States national phase of International Application No. PCT/EP2016/075765 filed Oct. 26, 2016, and claims priority to European Patent Application No. 15192135.0 filed Oct. 29, 2015, the disclosures of which are hereby incorporated in their entirety by reference.

BACKGROUND OF THE INVENTION

Field of the Invention

The invention refers to an infrared gas detection system, such as a non-dispersive infrared absorption detector (NDIR sensor).

Description of Related Art

Infrared gas analyzers detect infrared radiation passing through a gas sample. Typically, an IR gas analyzer comprises an infrared source, a measurement section such as a cuvette having a gas inlet and a gas outlet and an infrared sensor. The infrared source emits an IR radiation into and through the measurement section where it passes through the gas sample contained therein. The infrared sensor receives and senses the IR radiation passing through the gas sample. NDIR sensors measure the amount of infrared radiation in one or several wavelength ranges in the radiation passed through the gas to be analyzed. The selectivity of an NDIR sensor is determined by selecting the appropriate wavelength ranges to fit specific absorption lines of the respective gas to be measured. The measurement principle is based on the fact that specific gas components absorb infrared radiation. The absorption ranges are to be detected by the infrared gas analyzer.

The infrared sensor transduces the magnitude of variations in incoming IR radiation energy into an electrical signal. Some IR sensors employ piezo materials and are known as pyroelectric sensors. The piezo material absorbs incoming radiation causing a temperature shift which in turn induces a temporary electrical potential across the material that can be used as a measurement of the change in incoming radiation intensity.

Such infrared sensors, therefore, generally also react to different types of mechanical stress such as acceleration and pressure changes. This phenomenon is called microphony. The microphony phenomenon often determines the lower limits for detectable gas concentrations because below a certain amplitude of the measurement signal of the IR sensor, it cannot be determined, whether the measurement signal originates from a specific gas component or from mechanical stress, motion or vibration which is not caused by the gas. This is a particular problem of mobile or handheld detectors employing infrared gas analysis. Walking movements of the operator carrying the detector have a significant intensity in the frequency spectrum typically used for IR system modulation. If the detector probe hits an obstacle, such as a curbstone, this may also result in an amplitude of the electrical measurement signal of the infrared gas analyzer which might be misinterpreted as originating from a specific gas component.

The underlying problem of the invention is to increase the accuracy and sensitivity of gas detection systems employing infrared gas analysis.

SUMMARY OF THE INVENTION

According to a non-limiting embodiment of the invention, the infrared gas detection system of the invention comprises a gas inlet, an infrared gas analyzer connected to the gas inlet and a secondary gas sensor connected to the gas inlet. The system also comprises an evaluation device which evaluates the measurement signals from both the infrared gas analyzer and from the secondary gas sensor in such a way, that a specific type of gas is identified only if both the infrared measurement signal and the secondary measurement signal match with said gas type. The infrared gas analyzer may be of the type previously known in the prior art. The secondary gas sensor may be of any type of known gas sensor which is less sensitive to mechanical acceleration, motion or vibration than the infrared gas sensor. In particular, the secondary sensor does not need to be of a specific type. It can be quite non-selective. It only needs to be non-acceleration affected, or, at least less acceleration affected than the infrared gas analyzer. Thus, mostly any specific type of gas would generate a signal of the secondary sensor. The secondary sensor is thus used to generate a signal at the same point in time when the acceleration affected infrared gas analyzer also generates a signal. The coincidence in time of the gas-selective infrared signal and the non-gas-selective secondary sensor is used as an indication that the signal generated by the infrared gas analyzer is not generated by mechanical acceleration, but rather by a gas, namely the type of gas, to which the signal of the IR gas analyzer corresponds.

For example, the infrared gas analyzer may comprise a pyroelectric infrared sensor, a piezoelectric sensor or another type of sensor which senses accelerations, motion or vibration. The secondary gas sensor may contain at least one metal-oxide semiconductor (MOS) sensor, an $SnO_2$ sensor, a catalytic gate field effect sensor, an electrochemical sensor, a thermal conductivity sensor, a carbon nanotube sensor and/or a graphene based sensor.

Typically, the infrared gas analyzer comprises an infrared source, an absorption cuvette having an inlet connected to the gas inlet and an outlet, wherein the infrared sensor detects infrared radiation generated by the infrared source and passing through the absorption cuvette.

According to a non-limiting embodiment of the invention, the method of the invention for detecting gas components analyzed by an infrared gas analyzer and a secondary gas sensor as described above and defined in the claims, analyzes a gas component and detects the analyzed gas component as a specific gas component only, if the measurement signals of both the infrared gas analyzer and the secondary gas sensor coincide with said gas component. In other words, if both the IR gas analyzer and the secondary gas sensor generate signals at the same time or within a narrow range of time, this timing coincidence is used to exclude the possibility that the infrared gas analyzer reacts to mechanical vibration, acceleration or motion, but rather to a gas. Due to the high selectivity to specific gases or to a specific gas component, the type of gas can be determined from the selectivity of the IR gas analyzer.

In general, it might also be possible that the IR gas analyzer and the secondary gas sensor each react to an overlapping range of gases. If both sensors react, it may be determined that the gas must be within the overlapping range.

The measurement signal of the secondary gas sensor may be employed for detection of a specific gas component only, if the measurement signal of the infrared gas sensor is below a predetermined threshold. Said threshold may be an electrical signal amplitude corresponding to a specific acceleration measured by the infrared sensor. The threshold may be chosen such that the measurement signal of the infrared gas sensor above the predetermined threshold would sufficiently identify the specific gas component. Above the threshold, measurement signals of the infrared gas sensor which originate from accidental mechanical vibration would be low enough in order to be sufficiently differentiated from a signal caused by the specific gas component.

The measurement signal from the infrared gas analyzer may be employed as a reference signal for the secondary sensor, if the measurement signal from the infrared sensor indicates 0 ppm of a specific gas component. This enables an easy and safe real-time zero point calibration of the secondary sensor.

The invention is based on the idea to analyze the gas which is being analyzed by the infrared gas analyzer, also with a secondary gas sensor. The secondary gas sensor is less sensitive to mechanical acceleration, motion or vibration than the infrared gas sensor. The selectivity of the secondary gas sensor is lower than that of the infrared analyzer. Consequently, the secondary sensor reacts to several gas components. Typically, if the secondary gas sensor reacts to a specific gas component and generates a measurement signal above a predetermined threshold, it cannot be determined which gas component has caused this measurement signal.

The infrared gas analyzer, on the other hand, has a higher selectivity than the secondary sensor. However, if the infrared sensor generates a measurement signal amplitude below a certain threshold, it cannot be determined whether this signal amplitude results from a specific gas component or from mechanical acceleration or pressure changes. Therefore, the measurement signal from the secondary gas sensor is employed for the determination of the tested gas component below this threshold. This threshold may be referred to as selectivity threshold.

According to an embodiment of the invention, the secondary sensor analyzes the gas component which has previously been analyzed by the infrared gas analyzer. Above this selectivity threshold, mechanical acceleration or pressure changes do not affect the measurement signal of the infrared sensor in a critical way. This relates to typical mechanical accelerations or vibrations which occur during handheld measurement, such as vibrations from the walking operator or from collisions with curbstones.

The advantage of the invention is that the high selectivity of the infrared sensor is combined with the low sensitivity to acceleration and pressure changes of the secondary sensor. The disadvantage of the secondary sensor reacting to multiple gas components is overcome by the measurement signal of the highly selective infrared sensor. If both sensors react simultaneously or within the delay determined by the time constants of the system, this is used as an indication that a gas signal has been detected rather than a collision with a curbstone or other mechanical acceleration. The measurement signal from the infrared sensor can be used to identify the gas, when both the infrared sensor and the secondary gas sensor generate a measurement signal above a specific threshold.

The delay between the reactions of both sensors is determined by the time constant of the system. The delay is determined by the time needed to transport the sample between the two sensors and the reaction time of the sensor placed at the second position related to the direction of the flow, i.e. the sensor placed most downstream of the two. The delay can be calculated as follows:

$$\Delta t = \frac{V_{Transport}}{\varphi_{Sample}} + \tau_2$$

where:
$\Delta t$ is the delay time between signals exhibited by the first and second sensor named after their position in the gas flow direction,
$V_{Transport}$ is the internal volume in cubic centimeters (ccm) of the conduit leading the gas sample from the first sensor position to the second,
$\varphi_{Sample}$ is the flow rate of the sample gas moving in said conduit in ccm/second (s), and
$\tau_2$ is the reaction time of sensor number 2 (placed after sensor 1 in the flow direction).

For practical reasons this delay should be kept as low as possible and preferably below 1 s for an overall fast reaction time of the system. Typically achievable delay times are in the range of 0.2 to 3 s depending on sensor types and system architecture.

BRIEF DESCRIPTION OF THE DRAWINGS

FIG. 1 is a schematic diagram of non-limiting embodiments of the invention.

DESCRIPTION OF THE INVENTION

An embodiment of the invention is discussed below with reference to the FIGURE.

The gas detection system 10 comprises an infrared gas analyzer 12 and a secondary gas sensor 14. Both the IR gas analyzer 12 and the secondary gas sensor 14 analyze the same gas samples originating from the same sample gas inlet 16. The sample gas inlet 16 and a reference gas inlet 18 may be part of a handheld gas detector probe. This concept is described in U.S. Pat. No. 7,030,381 B2, the contents of which are incorporated herein by reference. The reference gas inlet 18 and the sample gas inlet 16 are both connected via separate gas conduits 22, 24, to a gas modulation valve 20 which switches between the reference gas conduit 22 originating from the reference gas inlet 18 and the sample gas conduit 24 originating from the sample gas inlet 16. The gas modulation valve 20 connects either of the conduits 22, 24 with a main gas conduit 26 through which the gas to be analyzed is conveyed to the infrared gas analyzer 12 and to the secondary gas sensor 14. Of course, the invention can also be employed in systems with only a sample gas inlet and no reference gas inlet or gas modulation valve.

The main gas conduit 26 contains a sample vacuum pump 28 conveying the gas to the analyzer 12. The gas which is pumped by the sample pump 28 is guided through the main gas conduit 26 into the inlet 29 of the absorption cuvette 30 of the infrared gas detector 12. The gas exits the cuvette 30 through an outlet 32. An infrared source 34 is located at one end of the cuvette 30 and separated from the entire volume of the cuvette 30 through which the gas passes by an optical window 35. At the opposite end of the cuvette 30, an optical filter 39 and an infrared sensor 36 are located and separated from the entire of the cuvette 30 through which the gas sample passes by an optical window 37. The optical windows 35, 37 may be made of Si, Ge or $CaF_2$ and are transparent for the infrared radiation from the source 34. The windows 35, 37 thereby separate the component 34, 36 and 39 from the gas flow path. The optical filter 39 is preferably a dichroic or interference filter restricting the wave length range passing through the window 37 and detected by the infrared sensor 36 to the characteristic wave length of the gas to be detected, for example methane. In general, the filter 39 should restrict the wave length range of the infrared radiation to a wave length range comprising the wave length of the gas to be detected while not comprising wave lengths of other characteristic gases.

Infrared radiation originating from the infrared source 34 radiates through the optical window 35 into the entire volume of the cuvette 30 and through the gas sample passing through the cuvette, and then through the optical window 37, the optical filter 39 and is received by the infrared sensor 36. The infrared sensor 36 is a pyroelectric sensor which generates an electrical signal in reaction to the received wavelength ranges of the infrared radiation.

The sample vacuum pump 28 could also be placed within the line 38 connecting the two sensors 12, 14. Alternatively, the pump 28 could also be placed after the secondary sensor 14. The advantage of locating the pump 28 within the main gas conduit 26 between the gas inlet 16 and the infrared gas detector 12 is that pressure drops in the cuvette due to varying restrictions in the sampling probes are avoided.

The gas sample exiting the outlet 32 is guided through the secondary gas conduit 38 to the secondary inlet 40 of the secondary sensor 14. The secondary gas sensor 14 is non-selective with regard to a specific gas component. The secondary gas sensor 14 generates an electrical signal in response to a wider range of gases or gas components.

The main idea of the invention is that the secondary sensor 14 is less selective to gases than the infrared gas analyzer 12 and the coincidence in time of the reactions of both sensors 36 and 14 is used as an indication that a gas has caused the reaction of the infrared gas detector 12.

An evaluation device which is not shown in the FIGURE receives the measurement signals from both the infrared gas analyzer 12 and from the secondary gas sensor 14. If the measurement signal from the infrared gas analyzer 12 is below a predetermined measurement threshold or selectivity threshold, it cannot be determined whether this signal results from a specific gas component or from a mechanical acceleration or vibration. In this case, the measurement signal generated by the secondary gas sensor 14 is also evaluated by the evaluation device. If the measurement signal from the secondary gas sensor 14 exceeds a certain threshold and if the measurement signals from both sensors 14, 36 coincide and/or match with a specific type of gas, this type of gas is considered as being detected by the gas detection system 10.

For example, a measurement signal from the secondary gas sensor 14 might be caused by any of four different gas components A, B, C or D, because the secondary gas sensor 14 is non-selective. This means, that the secondary gas sensor 14 detects whether any of these gases is present or not, no matter what type of gas is present. In this example, it cannot be determined whether the secondary gas sensor 14 reacts to gas component A, B, C or D. However, if the infrared gas analyzer 12 is selective to mechanical acceleration or pressure changes which can be caused by mechanical stress or by gas component A, it means that gas component A has been detected if both the gas analyzer 12 and the secondary gas sensor 14 generate a measurement signal.

A major advantage of the invention is that the secondary gas sensor 14 may be entirely non-gas selective. In general, the signal generated by the secondary gas sensor 14 is only used in order to determine whether the infrared gas analyzer 12 reacts to a gas or to acceleration or motion. The secondary gas sensor 14 is not used in order to identify the type of gas, but it is rather used in order to exclude the option that the IR gas analyzer 12 reacts to accidental motion or acceleration. The type of gas may be determined from the selectivity of the IR gas analyzer 12 itself. The coincidence in time of the reactions of the IR gas analyzer 12 and the secondary sensor 14 is, thus, of major importance for the invention.

The invention claimed is:

1. A method for detecting gas components analyzed by an infrared gas analyzer and a secondary gas sensor, comprising detecting an analyzed gas component as a specific gas component only, by evaluating when the measurement signals of both the infrared gas analyzer and the secondary gas sensor coincide with said gas component or coincide in time, wherein a measurement signal of the secondary gas sensor is employed for detection of the specific gas component only, by evaluating when a measurement signal of an infrared sensor of the infrared gas analyzer is below a predetermined threshold, and wherein the predetermined threshold is an electrical signal amplitude corresponding to a specific acceleration measured by the infrared sensor.

2. The method according to claim 1, wherein a measurement signal from the infrared gas analyzer is employed as a reference signal for determining a current 0 ppm baseline of the secondary gas sensor, when the measurement signal from an infrared sensor of the infrared gas analyzer indicates 0 ppm of a specific gas component.

* * * * *